(12) United States Patent
Matur et al.

(10) Patent No.: US 11,147,863 B2
(45) Date of Patent: Oct. 19, 2021

(54) MULTIVALENT PNEUMOCOCCAL CONJUGATE VACCINE

(71) Applicant: BIOLOGICAL E LIMITED, Telangana (IN)

(72) Inventors: Ramesh Venkat Matur, Hyderabad (IN); Nagarajan Thirumeni, Hyderabad (IN); Rajendar Burki, Hyderabad (IN); Narender Dev Mantena, Hyderabad (IN); Mahima Datla, Hyderabad (IN)

(73) Assignee: Biological E Limited

( * ) Notice: Subject to any disclaimer, the term of this patent is extended or adjusted under 35 U.S.C. 154(b) by 233 days.

(21) Appl. No.: 15/772,771

(22) PCT Filed: Jun. 21, 2016

(86) PCT No.: PCT/IN2016/000157
§ 371 (c)(1),
(2) Date: May 1, 2018

(87) PCT Pub. No.: WO2016/207905
PCT Pub. Date: Dec. 29, 2016

(65) Prior Publication Data
US 2019/0240308 A1  Aug. 8, 2019

(30) Foreign Application Priority Data

Jun. 23, 2015  (IN) .......................... 3140/CHE/2015

(51) Int. Cl.
| | | |
|---|---|---|
| *A61K 39/09* | (2006.01) | |
| *A61K 47/64* | (2017.01) | |
| *A61P 31/04* | (2006.01) | |
| *A61K 9/00* | (2006.01) | |
| *A61K 39/39* | (2006.01) | |
| *A61K 39/00* | (2006.01) | |

(52) U.S. Cl.
CPC .......... *A61K 39/092* (2013.01); *A61K 9/0019* (2013.01); *A61K 9/0043* (2013.01); *A61K 9/0053* (2013.01); *A61K 39/39* (2013.01); *A61K 47/646* (2017.08); *A61K 47/6415* (2017.08); *A61P 31/04* (2018.01); *A61K 2039/55505* (2013.01); *A61K 2039/6037* (2013.01)

(58) Field of Classification Search
None
See application file for complete search history.

(56) References Cited

U.S. PATENT DOCUMENTS

| | | | |
|---|---|---|---|
| 5,360,897 | A | 11/1994 | Anderson et al. |
| 5,614,382 | A | 3/1997 | Metcalf |
| 5,693,326 | A | 12/1997 | Lees |
| 7,862,823 | B1 | 1/2011 | Leroy |
| 7,955,605 | B2 | 6/2011 | Prasad |
| 8,192,746 | B2 | 6/2012 | Caulfield et al. |
| 8,465,749 | B2 | 6/2013 | Lee et al. |
| 8,557,250 | B2 | 10/2013 | Lee |
| 8,603,484 | B2 | 12/2013 | Prasad |
| 8,808,708 | B2 | 8/2014 | Hausdorff et al. |
| 2009/0017059 | A1 | 1/2009 | Biemans et al. |
| 2010/0074922 | A1 | 3/2010 | Biemans et al. |
| 2010/0239604 | A1 | 9/2010 | Biemans et al. |
| 2012/0321658 | A1 | 12/2012 | Biemans et al. |

FOREIGN PATENT DOCUMENTS

| | | |
|---|---|---|
| CN | 101590224 | 12/2009 |
| CN | 103623401 | 3/2014 |
| CN | 103656631 | 3/2014 |
| CN | 103656632 | 3/2014 |
| CN | 104069488 | 10/2014 |
| WO | WO 93/15760 | 9/1993 |
| WO | WO 95/08348 | 4/1995 |
| WO | WO 96/29094 | 10/1996 |
| WO | WO 2013/191459 | 12/2013 |
| WO | WO 2014/092377 | 6/2014 |
| WO | WO 2014/092378 | 6/2014 |
| WO | WO 2016/079755 | 5/2016 |

OTHER PUBLICATIONS

Anderson et al., "Non-interference between two protein carriers when used with the same polysaccharide for pneumococcal conjugate vaccines in 2-year-old children," Vaccine 21(13-14):1554-9 (publication date: Mar. 28, 2003).
Carpenter et al. "Preparation of heparin-glyceryl controlled-pore glass affinity media for the separation of alpha and beta-lipoproteins," Journal of Chromatography 573:132-135 (publication date: Jan. 1992).
Chu et al., "Further Studies on the Immunogenicity of Haemophilus influenzae Type b and Pneumococcal Type 6A Polysaccharide-Protein Conjugates," Infection and Immunity, Infect. Immunity 40(1):245-256 (publication date: Apr. 1983).
Hausdorff et al. "Do pneumococcal conjugate vaccines provide any cross-protection against serotype 19A?" BMC Pediatrics Biomed Central 10(1):4 (publication date: Feb. 2, 2010).
International Search Report and Written Opinion dated Jan. 12, 2017 for International Application No. PCT/IN2016/000157.
Kohn et al., "Procedures for the Analysis of Cyanogen Bromide-Activated Sepharose or Sephadex by Quantitative Determination of Cyanate Esters and Imidocarbonates," Anal Biochem 115:375-382 (1981).
Nurkka et al. "Immunogenicity and Safety of the Eleven Valent Pneumococcal Polysaccharide-Protein D Conjugate Vaccine in Infants," Ped. Inf. Dis. J., 23(11):1008-1014 (publication date: Nov. 2004).

(Continued)

*Primary Examiner* — Jennifer E Graser
(74) *Attorney, Agent, or Firm* — Perkins Coie LLP

(57) ABSTRACT

The present invention relates to a multivalent Pneumococcal conjugate vaccine (PCV) composition comprising: 1) at least 12 capsular polysaccharides selected from serotypes 1, 3, 4, 5, 6B, 7F, 9N, 9V, 15B, 14, 18C, 19A, 19F, 22F, 23F and 33F of *S. pneumoniae* activated with CDAP and conjugated to carrier protein selected from $CRM_{197}$, pneumococcal surface protein A (PspA), pneumococcal adhesin protein (PsaA) or combination thereof and 2) a pharmaceutically acceptable carrier, wherein the composition does not contain capsular polysaccharide from serotype 6A.

4 Claims, 2 Drawing Sheets

(56) References Cited

OTHER PUBLICATIONS

Park et al., "Differential Effects of Pneumococcal Vaccines against Serotypes 6A and 6C," The Journal of Infectious Diseases 198(12):1818-1822 (publication date: Dec. 15, 2008).
Wakselman et al. "1-Cyano-4-dimethylamino-pyridinium salts: new water-soluble reagents for the cyanylation of protein sulphydryl groups," J.C.S. Chem. Comm., 21-22 (publication date: Jan. 1, 1976).
Wilchek et al, "Affinity Chromatography," Meth. Enzymol. 104:3-55 (1984).
Wuorimaa et al. "Tolerability and immunogenicity of an eleven-valent pneumococcal conjugate vaccine in healthy toddlers," Pediatric Infectious Disease Journal 20(3):272-277 (publication date: Mar. 2001).
Yu et al., "Immunity to Cross-Reactive Serotypes Induced by Pneumococcal Conjugate Vaccines in Infants," Journal of Infectious Diseases, 180(5):1569-1576 (publication date: Nov. 1999).

MULTIVALENT PNEUMOCOCCAL CONJUGATE VACCINE

RELATED APPLICATIONS

This application is a 35 USC § 371 National Stage application of International Application No. PCT/IN2016/000157, entitled "MULTIVALENT PNEUMOCOCCAL CONJUGATE VACCINE," filed on Jun. 21, 2016, which claims the benefit of Indian Patent Application No. 3140/CHE/2015, filed Jun. 23, 2015, which are hereby incorporated by reference herein in their entirety.

FIELD OF INVENTION

The present invention relates to novel multivalent Pneumococcal conjugate vaccine composition and a method for the production thereof.

BACKGROUND OF INVENTION

*Streptococcus pneumoniae* (pneumococcus) is a Gram-positive bacteria responsible for considerable morbidity and mortality (particularly in the young and aged), causing invasive diseases such as pneumonia, bacteremia and meningitis, and diseases associated with colonization, such as acute Otitis media. The rate of pneumococcal pneumonia in the U.S. for persons over 60 years of age is estimated to be 3 to 8 per 100,000. In 20% of cases this leads to bacteremia, and other manifestations such as meningitis, with a mortality rate close to 30% even with antibiotic treatment.

Pneumococcus is encapsulated with a chemically linked polysaccharide which confers serotype specificity. There are more than 90 known serotypes of pneumococci, and capsule is the principal virulence determinant for pneumococci, as the capsule not only protects the inner surface of the bacteria from complement, but is itself poorly immunogenic.

Pneumococcal vaccines includes pneumococcal polysaccharide vaccine and pneumococcal conjugate vaccines. It is generally accepted that the protective efficacy of the commercialized pneumococcal polysaccharide vaccine is more or less related to the concentration of antibody induced upon vaccination; indeed, the 23 polysaccharides were approved and marketed under the trade name Pneumovax® 23 by Merck solely upon the immunogenicity of each component polysaccharide. Pneumovax® 23 comprises unconjugated polysaccharides belonging to serotypes 1, 2, 3, 4, 5, 6B, 7F, 8, 9N, 9V, 10A, 11A, 12F, 14, 15B, 17F, 18C, 19F, 19A, 20, 22F, 23F and 33F.

The multivalent pneumococcal polysaccharide vaccines that have been licensed for many years were proved valuable in preventing pneumococcal disease in adults, particularly, the elderly and those at high-risk. However, infants and young children respond poorly to unconjugated pneumococcal polysaccharides. The pneumococcal conjugate vaccine, Prevnar®, containing the 7 most frequently isolated serotypes (4, 6B, 9V, 14, 18C, 19F and 23F) causing invasive pneumococcal disease (IPD) in young children and infants at the same time, was first licensed in the United States in February 2000. Following universal use of Prevnar®-7 in the United States, there has been a significant reduction in IPD in children due to the serotypes present in Prevnar®-7. Due to the limitations in serotype coverage with Prevnar®-7 in certain regions of the world, a 13-valent conjugate vaccine was developed and approved under the trade name Prevenar-13® containing serotypes 1, 3, 4, 5, 6A, 6B, 7F, 9V, 14, 18C, 19A, 19F and 23F conjugated to $CRM_{197}$. The activation of the polysaccharides is accomplished by partial oxidation of adjacent (vicinal) hydroxyl groups in the carbohydrate repeat units using sodium periodate or periodic acid.

Ten valent pneumococcal vaccine was approved under the trade name Synflorix® containing polysaccharide serotypes 1, 4, 5, 6B, 7, 9, 14, 23F conjugated to protein D (PD), serotype 18C conjugated to tetanus toxoid (TT) and serotype 19F conjugated to diphtheria toxoid (DT). For conjugate preparation, coupling of each of the *S. pneumoniae* serotype polysaccharides to either PD, DT or TT is done utilizing CDAP (1-cyano-4-dimethylamino-pyridinium tetrafluoroborate) as chemical reagent under controlled pH.

U.S. Pat. No. 5,360,897 disclosed immunogenic conjugate comprising reductive amination product of an intact capsular polymer of the bacterial pathogen *S. pneumoniae* having at least two carbonyl groups and a bacterial toxin or toxoid, said conjugate comprising a cross-linked conjugate in which there is a direct covalent linkage between the capsular polymer and the toxin or toxoid.

U.S. Pat. No. 7,862,823 claims a multivalent conjugate vaccine composition with at least two different carrier proteins.

U.S. Pat. No. 7,955,605 disclosed a process of making immunogenic conjugate consisting 19A where the activated serotype 19A polysaccharide and carrier protein are re-suspended in dimethyl sulfoxide (DMSO) to form conjugate.

U.S. Pat. No. 8,603,484 disclosed a method of making multivalent immunogenic composition where serotype 3 is reacted with a mild acid to hydrolyze it, this hydrolyzed serotype is reacted with oxidizing agent in the presence of bivalent cations resulting in an activated serotype 3 and then it is conjugated with a carrier protein, which involves reacting this activated products with a reducing agent resulting in a serotype 3 polysaccharide: carrier protein conjugate.

U.S. Pat. No. 8,808,708 B2 disclosed a 13-valent immunogenic composition consisting polysaccharide-protein conjugates where serotypes consist of 1, 3, 4, 5, 6A, 6B, 7F, 9V, 14, 18C, 19A, 19F and 23F, and wherein the carrier protein is $CRM_{197}$.

U.S. Patent publication 2009/0017059 A1 disclosed an immunogenic composition where serotypes 19A and 19F are conjugated to different bacterial toxoids.

U.S. Patent publication 2010/0074922 A1 disclosed immunogenic composition containing 10 or more serotypes wherein 19F capsular saccharide is conjugated to diphtheria toxoid (DT), serotype 18C capsular saccharide is conjugated to tetanus toxoid and serotypes 1, 4, 5, 6B, 7F, 9V, 14 and 23F capsular saccharides are conjugated to Protein D from *Haemophilus influenzae*.

U.S. patent publication US 2010/0239604 disclosed composition comprising multivalent *S. pneumoniae* capsular saccharide conjugates wherein serotype 19A is conjugated to a first bacterial toxoid and 19F is conjugated to a second bacterial toxoid and 2-9 of the *S. pneumoniae* capsular saccharides are conjugated to protein D.

US Patent publication 2012/321658 A1 (2010) disclosed an immunogenic composition wherein serotypes 1, 3, 19A and 19F linked to a protein carrier(s) either directly or indirectly through a chemistry other than reductive amination, and one or more different saccharides is/are selected from a second group consisting of serotypes 4, 5, 6A, 6B, 7F, 9V, 14, 18C and 23F which is/are linked to a protein carrier(s) by reductive amination.

U.S. Pat. No. 8,192,746 disclosed a multivalent immunogenic composition having capsular polysaccharides from serotypes 1, 3, 4, 5, 6A, 6B, 7F, 9V, 14, 18C, 19A, 19F, 22F, 23F, and 33F conjugated to $CRM_{197}$.

WO 2013/191459 A1 disclosed a conjugated 15 valent composition comprising different serotypes of S. pneumoniae derived from a capsular polysaccharide 1, 2, 3, 4, 5, 6A, 6B, 7F, 9N, 9V, 14, 18C, 19A, 19F and 23F.

WO 2014/092378 A1 disclosed an immunogenic conjugate composition where 12 serotypes are selected from 1, 3, 4, 5, 6A, 6B, 7F, 9V, 14, 18C, 19A, 19F, and 23F and remaining one from 22F or 33F.

WO 2014/092377 A1 disclosed a 13 valent composition wherein 12 serotypes are selected from 1, 3, 4, 5, 6A, 6B, 7F, 9V, 14, 18C, 19A, 19F, and 23F and the last serotype is either 12 or 9N.

Chinese Patent Application Publication No. CN 101590224 described a 14-valent pneumococcal polysaccharide-protein conjugate vaccine containing serotypes 1, 2, 4, 5, 6A, 6B, 7F, 9N, 9V, 14, 18C, 19A, 19F and 23F.

Chinese Patent Application Publication No. CN 103623401 disclosed 14 multivalent pneumococcal capsular polysaccharide-protein conjugate composition wherein said 14 different blood serotype is 1, 3, 4, 5, 6A, 6B, 9V, 14, 18C, 19A, 19F, 22F, 23F and 33F.

Chinese Patent Application Publication No. CN 103656632 A disclosed multivalent pneumococcal capsular polysaccharide composition containing serotype 6A and at least one extra serotype selected from the group consisting of 1, 2, 3, 4, 5, 6B, 7F, 8, 9N, 10A, 11A, 12F, 14, 15B, 17F, 18C, 19A, 19F, 20, 22F, 23F and 33F. The multivalent pneumococcal capsular polysaccharide composition provided herein can be used for inducing an organism to generate humoral immunity and can generate a relatively good protecting effect for infectious diseases caused by the 24 common serotype of pneumococci.

Chinese Patent Application Publication No. CN 103656631 A disclosed multivalence pneumococcus capsular polysaccharide-protein conjugate composition and a preparation method thereof. The conjugate composition is prepared from capsular polysaccharides of pneumococcus of 24 different serotypes and a carrier protein in a covalent linkage manner, wherein the 24 different serotypes are 1, 2, 3, 4, 5, 6A, 6B, 7F, 8, 9N, 9V, 10A, 11A, 12F, 14, 15B, 17F, 18C, 19A, 19F, 20, 22F, 23F and 33F.

Chinese Patent Application Publication No. CN 104069488 A disclosed multivalent pneumococcus capsular polysaccharides of 14 different serotypes and carrier protein, wherein the 14 serotypes include 1, 4, 5, 6A, 6B, 7F, 9V, 14, 18C, 19A, 19F, 22F, 23F and 33F.

Cyanylating agents are well known in art (Wilcheck et al., Affinity chromatography. Meth. Enzymol., 104C:3-55; Wakelsman et al., J. C. S Chem. Comm., 1976:21 (1976). It was reported as a mild reagent that can be used for modifying protein cysteine groups. Whereas it was Kohn et al., (Anal. Biochem, 115:375, 1981) who compared CDAP, N-cuanotriethyl-ammonium tetrafluoroborate (CTEA) and p-nitrophenylcyanate (Pnpc). This comparison was done to compare the activation of agarose by these agents. CDAP has also been used to activate insoluble particles such as Sepharose and glyceryl-controlled pore glass (Carpenter et al., Journal of Chromatography, 573:132-135, 1992)

U.S. Pat. No. 5,693,326 gives a generalised method for preparing a conjugate vaccine wherein for activating viral, fungal or bacterial polysaccharides, organic cyanylating agent is used selected from the group 1-cyano-4-(dimethylamino)-pyridinium tetrafluoroborate, N-cyanotriethyl-ammonium tetrafluoroborate, and p-nitrophenylcyanate, to form an activated carbohydrate and then coupled to the protein or carrier protein.

U.S. Pat. No. 8,465,749 disclosed a method for preparing a conjugate vaccine by reacting a polysaccharide with CDAP and reacting a protein with hydrazine or adipic acid dihydrazide with specific pH range.

U.S. Pat. No. 8,557,250 B2 disclosed a method which comprises contacting the mixture of the plurality of cyanate activated immunogenic distinct polysaccharides with at least one hydrazide activated protein.

Anderson P et al, (2003, Vaccine; 21 (13-14):1554-9) discloses a comparative study of tetravalaent conjugate vaccines with each polysaccharide types 6A, 14, 19F, and 23F separately coupled to tetanus toxoid or diphtheria $CRM_{197}$ or a mixture of halved doses of polysaccharide types 6A, 14, 19F, and 23F separately coupled to tetanus toxoid and diphtheria $CRM_{197}$.

Anticipating multivalent polysaccharide conjugate vaccines of the future to be used in infancy, this strategy would have two hypothetical advantages worth further investigation—avoiding "carrier epitopic overload" by reducing each carrier dosage and recruiting T-helper activity by both carriers for each polysaccharide.

Wuorimaa et al. (2001, The Paediatric Infectious Disease Journal, Volume 20(3), pp 272-277) discloses a study to assess the tolerability and immunogenicity in healthy toddlers of an 11-valent pneumococcal conjugate vaccine that uses both tetanus and diphtheria toxoids as carriers.

Gatchalian et al. (2001, 17th Annual Meeting of the Eur. Soc. Paed. Inf. Dis (ESPID), poster number 4, NA Poster Session 1, Istanbul Turkey) discloses OPA results from infants who had received doses of the 11-valent vaccine failed to show antibody responses for serotype 3 at levels comparable to other tested serotypes.

Nurkka et al. (2004, Ped. Inf. Dis. J., 23:1008-1014) discloses a study of the immunogenicity and safety of an 11-valent pneumococcal protein D conjugate vaccine where no priming effect was observed for serotype 3 in infants who had received three doses of the vaccine followed by a booster dose of either the same vaccine or a pneumococcal polysaccharide vaccine.

The above mentioned references disclosed polysaccharides belonging to various serotypes and their conjugation with carrier proteins following different methods. But there is a need to have a new serotype composition in view of the serotype prevalence of a given region and their production in a simple and efficient manner. The inventors of the present invention found that the combination of serotypes 22F and 33F together with other serotypes without 6A improves the immunogenicity towards serotypes.

Objective of the Invention

The main objective of the present invention is to provide a novel multivalent polysaccharide conjugate vaccine.

Yet another objective of the present invention is to provide a process for preparing the novel multivalent polysaccharide conjugate vaccine.

SUMMARY OF INVENTION

The present invention relates to a multivalent Pneumococcal conjugate vaccine (PCV) composition comprising:
1) at least 12 capsular polysaccharides selected from serotypes 1, 3, 4, 5, 6B, 7F, 9N, 9V, 15B, 14, 18C, 19A, 19F, 22F, 23F and 33F of S. pneumoniae activated with CDAP and conjugated to carrier protein selected from CRM$_{197}$, pneumococcal surface protein A (PspA), pneumococcal adhesin protein (PsaA) or combination thereof and 2) a pharmaceutically acceptable carrier, wherein the composition does not contain capsular polysaccharide from serotype 6A.

The present invention relates to a multivalent Pneumococcal conjugate vaccine (PCV) composition comprising:
(1) at least 14 capsular polysaccharides selected from serotypes 1, 3, 4, 5, 6B, 7F, 9N, 9V, 14, 15B, 18C, 19A, 19F, 22F, 23F and 33F of S. pneumoniae activated with CDAP and conjugated to CRM$_{197}$, PspA, PsaA or combination thereof and
(2) a pharmaceutically acceptable carrier, wherein the composition does not contain capsular polysaccharide from serotype 6A.

DETAILED DESCRIPTION OF THE INVENTION

Figure 1:
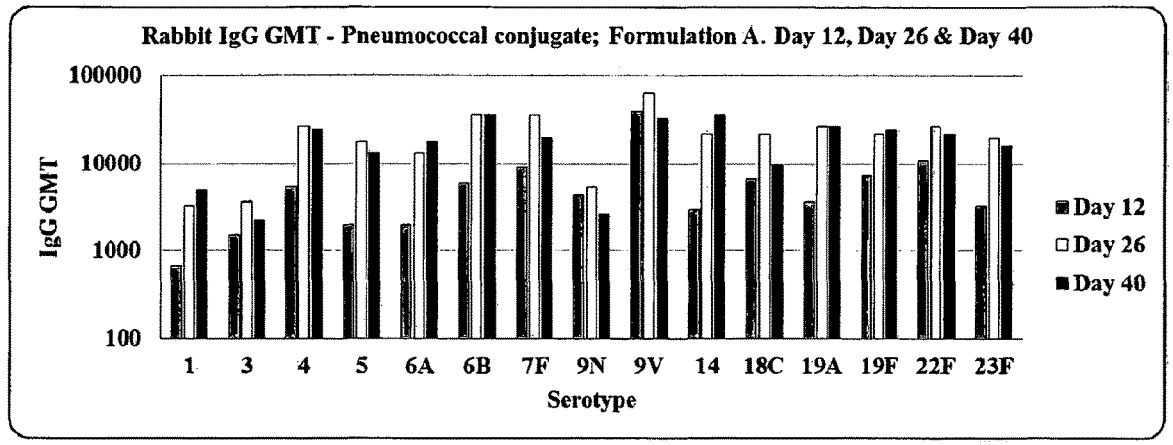
FIG. 1. Titre of IgG to individual pneumococcal capsular polysaccharides induced by Formulation A in rabbits as measured by Indirect ELISA.

The present invention provides an immunogenic multivalent serotype composition, more specifically a conjugated pneumococcal vaccine composition comprising at least 13 pneumococcal polysaccharide serotypes which are individually conjugated to a pharmaceutically acceptable carrier protein CRM$_{197}$, wherein the composition does not contain capsular saccharide from serotype 6A. Serotypes 6A and 6B are structurally and serologically similar. Capsules of serotypes 6A and 6B are isopolymers differing only in the rhamnose-ribitol linkage, because of which antibodies specific to serotype 6B capsular polysaccharide cross-react with serotype 6A capsular polysaccharide. Therefore, exclusion of serotype 6A, provides a leverage for including an additional epidemiologically relevant serotype for broadening the protection against pneumococcal disease without having to expand the valence of multivalent PCV.

The present invention also provides an immunogenic multivalent serotype composition, wherein the capsular polysaccharides from serotypes 1, 3, 4, 5, 6B, 7F, 9N, 9V, 14, 15B, 18C, 19A, 19F, 22F, 23F and 33F of S. pneumoniae are conjugated to a carrier protein CRM$_{197}$, wherein the composition does not contain capsular polysaccharide from serotype 6A. Further, the present invention may additionally contain one or more serotypes selected from 6C, 8, 10A, 11A, 12F, 15A, 23A, 23B and 35B of S. pneumoniae.

Preferably, the present invention provides 13 valent, 14 valent or 15 valent immunogenic composition, wherein the composition does not contain capsular polysaccharide from serotype 6A.

Serotype 22F and serotype 3 are the most commonly found serotypes causing IPD due to expansion of certain clonal types. Serotype 33F is also amongst the most commonly encountered serotypes.

CRM$_{197}$ is a variant of diphtheria toxin and is by itself non-toxic (i.e., toxoid) for use in vaccines. CRM$_{197}$ is isolated from cultures of Corynebacterium diphtheriae strain C7 (β197) grown in casamino acids and yeast extract-based medium. CRM$_{197}$ may be prepared recombinantly in accordance with the methods described in U.S. Pat. No. 5,614,382. Alternatively, CRM$_{197}$ is prepared recombinantly in accordance with the methods known in the literature or according to the method disclosed in our PCT publication WO 2016/079755. CRM$_{197}$ may be purified by ultrafiltration, ammonium sulphate precipitation, and ion-exchange chromatography, methods well known in art.

The polysaccharide may be extracted from the microorganism according to conventional methods and purified likewise. This polysaccharide may be used in the native form after extraction/purification. Alternatively, it may be fragmented in order to obtain a polysaccharide having an average molecular weight less than that of the polysaccharide originally extracted.

The polysaccharide thus derived are then activated by CDAP and then conjugated with carrier proteins such as CRM$_{197}$, PspA, PsaA or combination thereof.

In another embodiment, the conjugation method depends on activation of the saccharide with CDAP to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in WO 93/15760, WO 95/08348 and WO 96/29094; and Chu et al., 1983, Infect. Immunity 40:245-256.

After conjugation of the capsular polysaccharide to the carrier protein, the polysaccharide-protein conjugates are purified (enriched with respect to the amount of polysaccharide-protein conjugate) by a variety of techniques. These techniques include concentration/diafiltration operations, precipitation/elution, column chromatography, and depth filtration.

After the individual glycoconjugates are purified, they are compounded to formulate the immunogenic composition of the present invention, which can be used as a vaccine.

In a preferred embodiment, the invention provides a multivalent Pneumococcal conjugate vaccine (PCV) composition comprising
a) at least 13 capsular polysaccharides selected from serotypes 1, 3, 4, 5, 6B, 7F, 9N, 9V, 14, 15B, 18C, 19A, 19F, 22F, 23F and 33F of Streptococcus pneumoniae activated with CDAP and conjugated to CRM$_{197}$, PspA, PsaA or combination thereof and
b) A pharmaceutically acceptable carrier, wherein the composition does not contain capsular saccharide from serotype 6A.

In another embodiment, amount of polysaccharide from each of the serotypes 1, 3, 4, 5, 6B, 7F, 9N, 9V, 14, 15B, 18C, 19A, 19F, 22F, 23F and 33F is 1 to 10 µg, preferably, 1 to 5 µg conjugated to 3 to 30 µg of $CRM_{197}$ carrier protein. The ratio of polysaccharide to carrier protein is 0.3:3.

A composition according to the invention may be manufactured conventionally. In particular, it may be formulated with a pharmaceutically acceptable diluent or vehicle, e.g. water or a saline solution. In addition, the composition may contain ingredients such as a buffer, a preservative or a stabilizer, polysorbate, an adjuvant such as an aluminum compound, e.g. an aluminium hydroxide, an aluminium phosphate or an aluminium hydroxyphosphate, and, a lyophilization excipient. In general, these products may be selected as a function of the mode and route of administration and based on standard pharmaceutical practices.

The composition of the present invention can be formulated in a form of a unit dose vial, multiple dose vial, or pre-filled syringe. The composition may further comprise of one or more preservative(s) selected from thiomersal, 2-phenoxyethanol and the like. The amount of preservative may range from 4 to 20 mg/mL.

A composition according to the invention may be administered by any conventional route which is used in the field of vaccines, in particular by the systemic, i.e. parenteral route, e.g. by the subcutaneous, intramuscular, intradermal or intravenous route, or by the mucosal route, e.g. by the oral or nasal route.

"Effective amount" of a composition of the invention refers to a dose required to elicit antibodies that significantly reduce the likelihood or severity of infectivity of S. pneumoniae during a subsequent challenge.

In one embodiment, the present invention further provides an immunogenic composition administered as a single 0.5 mL dose formulated to contain: 2 µg of each polysaccharide; 30-40 µg $CRM_{197}$ carrier protein; 0.2 to 1 mg of aluminum phosphate adjuvant; sodium chloride and buffer as excipients.

In yet another preferred embodiment, the present invention provides a serotype composition for formulating a 13 valent PCV comprising;
 conjugation of the pneumococcal capsular polysaccharides of known size belonging to 13 serotypes activated utilizing CDAP, individually to an immunogenic carrier protein $CRM_{197}$,
 diafiltration of the individual monovalent pneumococcal conjugates followed by purification using size exclusion chromatography,
 analysis of the fractions by SEC-HPLC and pooling of fractions containing monovalent pneumococcal conjugates before filter sterilization using 0.2 µm filter and formulation of the 13 valent PCV using 13 monovalent pneumococcal conjugates; 4.4 µg for serotype 6B; 2.2 µg for rest of the serotypes and Adju-Phos® adjuvant together with appropriate excipient and buffer followed by aseptic filling.

The serotype composition of PCV 13 contains serotypes 1, 3, 4, 5, 6B, 7F, 9V, 14, 18C, 19A, 19F, 22F and 33F.

In yet another preferred embodiment, the present invention provides a serotype composition for formulating a 14 valent PCV comprising;
 conjugation of pneumococcal capsular polysaccharides of known size belonging to 13 serotypes activated utilizing CDAP, individually to an immunogenic carrier protein $CRM_{197}$,
 diafiltration of the individual monovalent pneumococcal conjugates followed by purification using size exclusion chromatography,
 analysis of the fractions by SEC-HPLC and pooling of fractions containing monovalent pneumococcal conjugates before filter sterilization using 0.2 µm filter and formulation of the 14 valent PCV using monovalent pneumococcal conjugates; 4.4 µg for serotype 6B; 2.2 µg for rest of the serotypes and Adju-Phos® adjuvant together with appropriate excipient and buffer followed by aseptic filling.

The serotype composition of PCV 14 contains serotypes 1, 3, 4, 5, 6B, 7F, 9V, 14, 18C, 19A, 19F, 22F, 23F and 33F.

Carrier proteins are preferably proteins that are non-toxic and non-reactogenic and obtainable in sufficient amount and purity. A carrier protein can be conjugated or joined with a S. pneumoniae polysaccharide to enhance immunogenicity of the polysaccharide. Carrier proteins should be amenable to standard conjugation procedures. In a particular embodiment of the present invention, $CRM_{197}$ is used as the carrier protein. In one embodiment, each capsular polysaccharide is conjugated to a single carrier protein. In another embodiment, the capsular polysaccharides are conjugated to two or more carrier proteins.

In another embodiment, the capsular polysaccharides from S. pneumoniae may be conjugated to one or more carrier proteins such as inactivated bacterial toxins such as tetanus toxoid, pertussis toxoid; cholera toxoid, exotoxin A from Pseudomonas aeruginosa, bacterial outer membrane proteins such as outer membrane complex c (OMPC), porins, transferrin binding proteins, pneumolysin, pneumococcal surface protein A (PspA), pneumococcal adhesin protein (PsaA), C5a peptidase from Group A or Group B streptococcus, or Haemophilus influenzae protein D. Other proteins, such as ovalbumin, keyhole limpet hemocyanin, (KLH), bovine serum albumin (BSA) or purified protein derivative of tuberculin (PPD) may also be used as carrier proteins.

The amount of conjugate in each vaccine dose is selected as an amount that induces an immunoprotective response without significant, adverse effects. Such an amount may vary depending upon the pneumococcal serotype. Generally, each vaccine dose will comprise 0.1 to 50 µg of each polysaccharide, preferably 0.1 to 10 µg, and more preferably 1 to 5 µg.

In a preferred embodiment of the present invention, the PCV is a 14 valent sterile liquid formulation consisting of capsular polysaccharides of serotypes 1, 3, 4, 5, 6B, 7F, 9V, 14, 18C, 19A, 19F, 22F, 23F and 33F individually conjugated to $CRM_{197}$. Each 0.5 mL dose is formulated to contain: 2 µg of each polysaccharide, except for 6B at 4 µg; about 32 µg $CRM_{197}$ carrier protein; 0.125 mg of elemental aluminum (0.5 mg aluminum phosphate) adjuvant; and sodium chloride and L-histidine buffer.

In yet another preferred embodiment of the present invention, the PCV is a 13 valent sterile liquid formulation consisting of capsular polysaccharides of serotypes 1, 3, 4, 5, 6B, 7F, 9V, 14, 18C, 19A, 19F, 22F and 33F individually conjugated to $CRM_{197}$. Each 0.5 mL dose is formulated to contain: 2 µg of each polysaccharide, except for 6B at 4 µg; about 32 µg $CRM_{197}$ carrier protein; 0.125 mg of elemental aluminum (0.5 mg aluminum phosphate) adjuvant; and sodium chloride and L-histidine buffer.

In yet another preferred embodiment of the present invention, the PCV is a 13 valent sterile liquid formulation consisting of capsular polysaccharides of serotypes 1, 3, 4, 5, 6B, 7F, 9V, 14, 18C, 19F, 23F and 33 individually conjugated to CRM$_{197}$. Each 0.5 mL dose is formulated to contain: 2 µg of each polysaccharide, except for 6B at 4 µg; about 32 µg CRM$_{197}$ carrier protein; 0.125 mg of elemental aluminum (0.5 mg aluminum phosphate) adjuvant; and sodium chloride and L-histidine buffer.

According to the methods of the present invention, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

The present invention also provides a method of inducing an immune response to a S. pneumoniae capsular polysaccharide conjugate, comprising administering to a human an immunologically effective amount of the above multivalent immunogenic composition.

Effective amount here refers to a dose which is sufficient or most likely to elicit antibodies such that the immunized subject has reduced severity of infection. The following examples are provided to illustrate the invention and are merely for illustrative purpose only and should not be construed to limit the scope of the invention.

Example 1

Conjugation of Individual Pneumococcal Polysaccharide to Carrier Protein to Form Polysaccharide-CRM$_{197}$ Conjugates Polysaccharide Size Reduction:

In the first step, the polysaccharide (Ps) solution was passed through a high pressure homogenizer to reduce the molecular size of the polysaccharide followed by a concentrating and diafiltration step, using 100 kDa MWCO membrane. The sized polysaccharide produced thus was used for conjugation.

Activation of Polysaccharide and Conjugation with Carrier Protein:

Approximately, 1:1 ratio of polysaccharide and (6.0 mL of Ps, concentration of 10 mg/mL) CDAP (100 mg/mL in Acetonitrile (w/v)) was mixed in a glass vial and stirred for 1 min. Adjusted the pH of polysaccharide to 9.25 with 0.2M Triethylamine and stirred for 3 min at room temperature (RT). Slowly added (4.0 mL of conc. 15.0 mg/mL) CRM$_{197}$ to the activated polysaccharide to a ratio of 1:1.5 (Ps: Carrier protein). Adjusted the pH of the reaction to ~9.05 with 0.2M Triethylamine and continued the reaction under stirring for 5 hours at RT and finally quenched the reaction by adding excess concentration of glycine.

The reaction mixture was diafiltered using 100 kDa MWCO membrane and purified by size-exclusion chromatography. The fractions were analysed by SEC-HPLC and fractions containing conjugates were pooled and sterile filtered with 0.2 µm filters. This material was called monovalent conjugate bulk. All monovalent conjugate bulks for 14 serotypes were generated with similar process.

Example 2

Formulation of Multivalent Polysaccharide-CRM$_{197}$ into Vaccine

Three individual formulations namely, formulation A (13 valent: 1, 3, 4, 5, 6B, 7F, 9V, 14, 18C, 19A, 19F, 22F and 23F), formulation B (13 valent: 1, 3, 4, 5, 6B, 7F, 9V, 14, 18C, 19A, 19F, 23F and 33F) and formulation C (14 valent: 1, 3, 4, 5, 6B, 7F, 9V, 14, 18C, 19A, 19F, 22F, 23F and 33F) were prepared. In the above formulations, according to their composition 2.2 µg of each monovalent conjugate sterile bulk of 13 serotypes (1, 3, 4, 5, 7F, 9V, 14, 18C, 19A, 19F, 22F, 23F and 33F) and 4.4 µg of 6B monovalent conjugate sterile bulks were accurately measured. Each monovalent bulk conjugate, was slowly transferred (drop wise) one by one to the blending vessel, under continuous stirring (~150 rpm) and continued the stirring for 2 minutes at pH 6.5.

To the above mix Adju-Phos® was accurately measured and slowly transferred drop wise to the above blending vessel, under continuous stirring (~150 rpm) to the final concentration of Al$^{+3}$ to 1 mg/mL. After complete addition of the Adju-Phos®, the system was left under stirring for 2 minutes. The final pH of the solution was adjusted to 5.8±0.2 and continued stirring for 2 hours at around 150 rpm/5°±3° C. in a refrigerator. After completion of stirring, the vaccine was aseptically filled into vials inside a laminar air flow unit and stored at 5°±3° C. chamber.

Example 3

Immunogenicity Studies

Immunogenicity of pneumococcal conjugate formulations prepared according to the present invention was assessed in rabbit model of immunity. Five groups of female rabbits (adult, nulliparous and non-pregnant; 2.0 to 2.5 kg body weight) with a group size of seven were recruited for this study. Three formulations viz. Formulation A, Formulation B, Formulation C; a comparator vaccine (Prevnar 13™) and placebo were included in this study (Table 1). The rabbits were given single human dose equivalent irrespective of valence of the formulations with a dose volume of 0.5 ml. Each group of rabbits received 3 doses at an interval of 14 days, using the respective formulation through intramuscular route on days 1, 15 and 29 after appropriately preparing the site. They were humanely test bled on days 0, 12, 26 and 40, precisely 11 days after the administration of formulations. The serum samples were separated from clotted blood samples before storing them at −20° C. as aliquots. The serum samples were designated as preimmune serum (PIS; day 0), immune serum—post dose 1 (PD1; day 12), immune serum—post dose 2 (PD2; day 26) and immune serum—post dose 3 (PD3; day 40).

TABLE 1

Details of rabbit treatment groups chosen for immunogenicity assessment.

| | | Group | | Schedule | |
|---|---|---|---|---|---|
| S. No | Formulation | Group | size | Immunization | Bleeding |
| 1 | Formulation A | I | 7 | Day 1, Day 15 | Day 0, Day 12, |
| 2 | Formulation B | II | 7 | & Day 29 | Day 26 & |
| 3 | Formulation C | III | 7 | | Day 40 |
| 4 | Prevnar 13 ™ | IV | 7 | | |
| 5 | Placebo | V | 7 | | |

Figure 2:
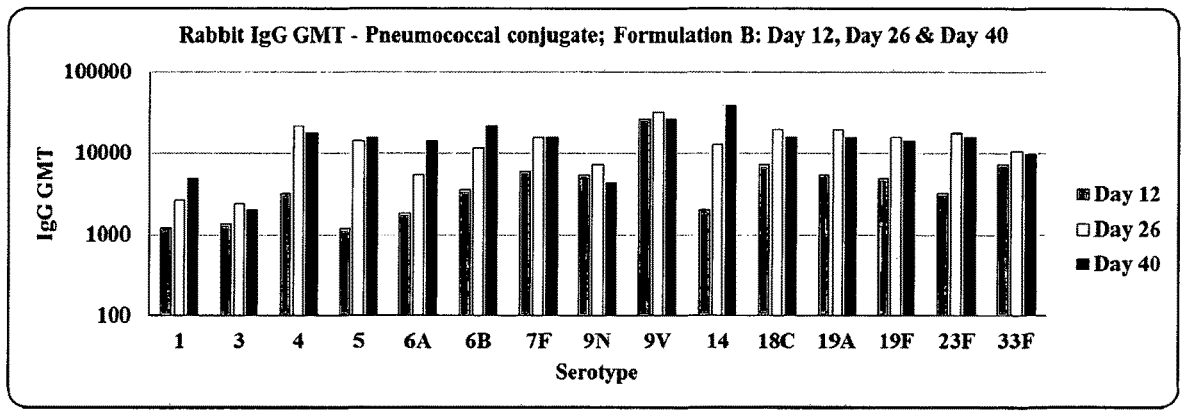
FIG. 2. Titre of IgG to individual pneumococcal capsular polysaccharides induced by Formulation B in rabbits as measured by Indirect ELISA.
Figure 3:
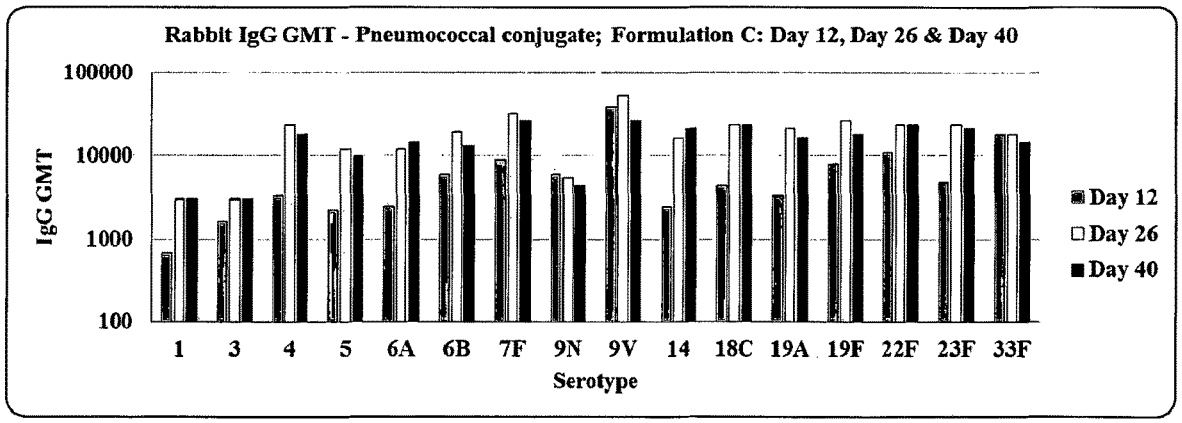
FIG. 3. Titre of IgG to individual pneumococcal capsular polysaccharides induced by Formulation C in rabbits as measured by Indirect ELISA.
Figure 4:
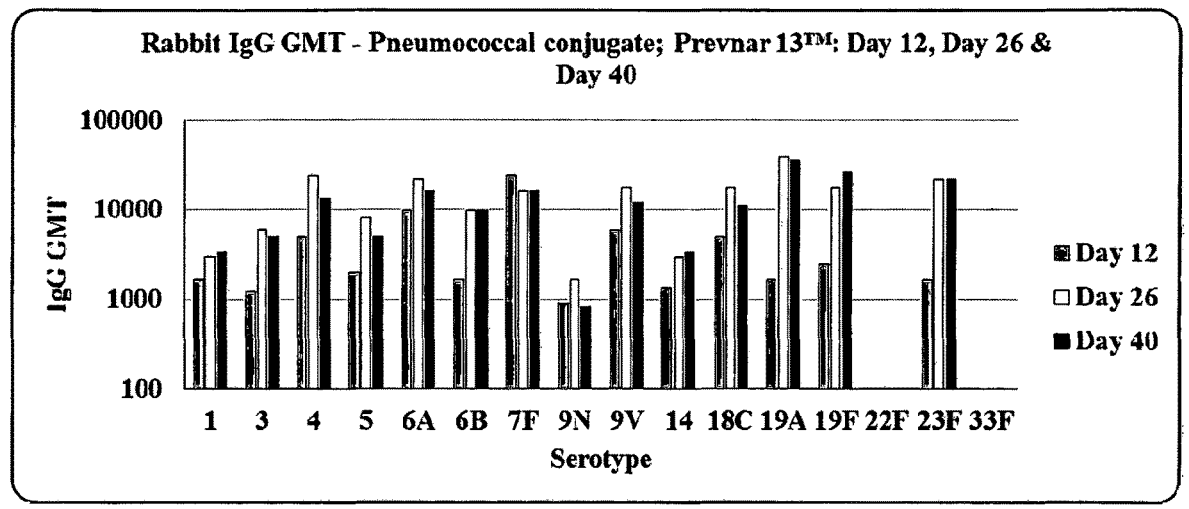
FIG. 4. Titre of IgG to individual pneumococcal capsular polysaccharides induced by Prevnar 13™ in rabbits as measured by Indirect ELISA.
Figure 5:
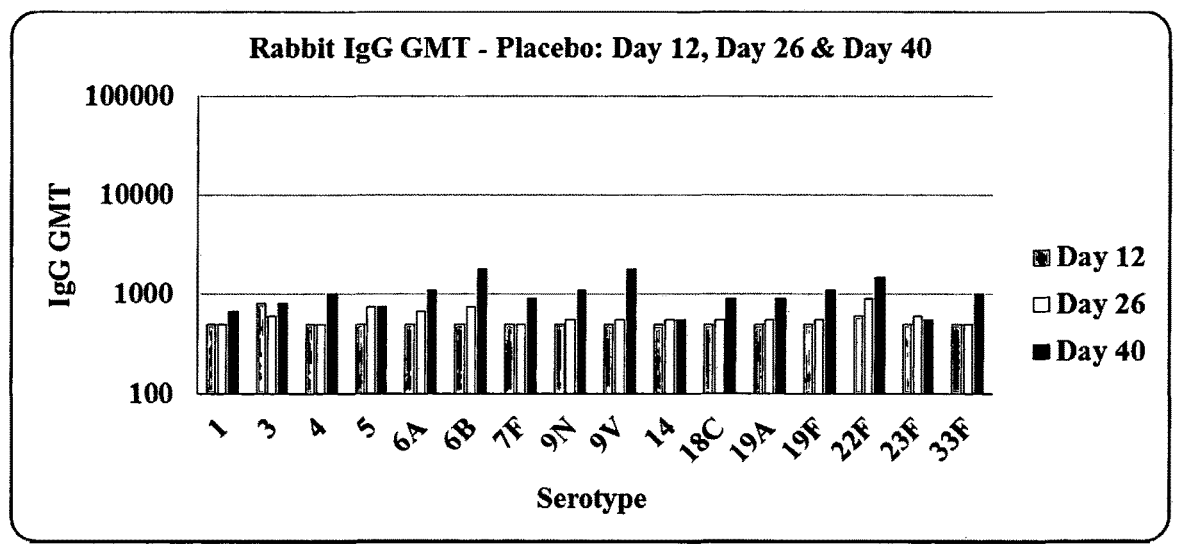
FIG. 5. Titre of IgG to individual pneumococcal capsular polysaccharides induced by Placebo in rabbits as measured by Indirect ELISA.

Titre of IgG to individual pneumococcal capsular polysaccharides (CPS) was measured by using ELISA, essentially following the standardized WHO ELISA protocol with slight modifications. Nunc Maxisorp® plates were used for immobilizing purified pneumococcal CPS sourced from ATCC, USA/Staten serum Institut, Denmark. The 007sp international pneumococcal reference serum known to contain anti-CPS IgG for 23 serotypes of 23 valent pneumococcal polysaccharide vaccine was used as a positive control. The non-functional cell wall polysaccharide (CWPS) reactive IgG was depleted by adsorbing the test and control serum samples with CWPS Multi™ as per the manufacturer's instruction before testing them by Indirect ELISA. Recombinant protein A/G peroxidase conjugate which combines the binding specificity of protein A and protein G was used for universal detection of rabbit and human IgG. Anti-CPS IgG titre for individual rabbits from a given group was determined based on cut-off which was calculated using the formula, [Mean OD of Blank×2]. Finally, the geometric mean titre (GMT) of anti-CPS IgG induced by Formulation A, Formulation B, Formulation C, Prevnar 13™ and Placebo was calculated (FIGS. 1-5).

The invention claimed is:

1. A multivalent Pneumococcal conjugate vaccine (PCV) composition consisting of:
   a) 14 capsular polysaccharides from serotypes 1, 3, 4, 5, 6B, 7F, 9V 14, 18C, 19A, 19F, 22F, 23F and 33F of *S. pneumoniae* activated with 1-cyano-4-dimethylaminopyridinium tetrafluoroborate (CDAP) and conjugated to $CRM_{197}$; and
   b) a pharmaceutically acceptable carrier,
      wherein the PCV composition does not contain capsular polysaccharide from serotype 6A.

2. The PCV composition of claim 1, wherein each of the serotypes is present in the PCV composition in an amount of 1 to 10 µg.

3. The PCV composition of claim 1, wherein an amount of $CRM_{197}$ conjugated to the 14 capsular polysaccharides is 3 to 30 µg.

4. The PCV composition of claim 1, wherein a single 0.5 mL dose of the PCV composition comprises 2 µg of each of the 14 capsular polysaccharides, 30 to 40 µg of $CRM_{197}$, 0.2 to 1 mg of aluminum phosphate adjuvant, sodium chloride, and a buffer.

* * * * *